US008166800B2

(12) United States Patent
Ieda et al.

(10) Patent No.: US 8,166,800 B2
(45) Date of Patent: May 1, 2012

(54) GAS CONCENTRATION DETECTION APPARATUS AND GAS CONCENTRATION DETECTION SYSTEM

(75) Inventors: Norikazu Ieda, Aichi (JP); Yoshinori Inoue, Aichi (JP); Hiroyuki Tsukada, Aichi (JP); Masahiro Tanaka, Dusseldorf (DE)

(73) Assignee: NGK Spark Plug Co., Ltd., Aichi (JP)

( * ) Notice: Subject to any disclaimer, the term of this patent is extended or adjusted under 35 U.S.C. 154(b) by 427 days.

(21) Appl. No.: 12/549,108

(22) Filed: Aug. 27, 2009

(65) Prior Publication Data
US 2010/0050743 A1 Mar. 4, 2010

(30) Foreign Application Priority Data
Aug. 27, 2008 (JP) ................................ 2008-218738

(51) Int. Cl.
*G01N 7/00* (2006.01)
(52) U.S. Cl. ...................................................... 73/31.05
(58) Field of Classification Search .................. None
See application file for complete search history.

(56) References Cited

U.S. PATENT DOCUMENTS
3,801,972 A * 4/1974 Kim et al. .................... 340/510

FOREIGN PATENT DOCUMENTS
JP         2006-275628 A    10/2006
* cited by examiner

*Primary Examiner* — Hezron E Williams
*Assistant Examiner* — Alex Devito
(74) *Attorney, Agent, or Firm* — Sughrue Mion, PLLC

(57) ABSTRACT

A gas concentration detection apparatus and system including a gas sensor. Voltage Vd generated across detection resistor Rd through which pump current Ip flows is differentially amplified by OP1, and offset voltage Vofs is superposed thereon to obtain a detection voltage Vout. The amplification factor applied to the differential amplification of the voltage Vd is changed by turning switch SW3 on and off. When switch SW2 is turned on, the input terminal potentials of the operational amplifier OP1 are equalized, so that voltage Vofs is output as the detection voltage Vout. The detection voltage Vout contains an error attributable to the electronic components which form the circuit. The detection voltage Vout containing the error when SW2 is turned on is acquired as a correction voltage for each amplification factor, and is used for correction at the time of detection of the concentration so as to cancel the error.

4 Claims, 4 Drawing Sheets

GAS CONCENTRATION DETECTION APPARATUS AND GAS CONCENTRATION DETECTION SYSTEM

BACKGROUND OF THE INVENTION

1. Field of the Invention

The present invention relates to a gas concentration detection apparatus which detects the concentration of a specific gas component in a gas of interest by measuring a current which flows through a gas sensor and whose magnitude changes in accordance with the concentration of the specific gas component. The present invention also relates to a gas concentration detection system which combines the gas sensor and the gas concentration detection apparatus.

2. Description of the Related Art

Conventionally, a gas sensor has been known which is installed in an exhaust passage of an internal combustion engine, such as an automotive engine, and which detects the concentration of a specific gas component (for example, oxygen) in exhaust gas. This gas sensor detects the oxygen concentration and ultimately the air fuel ratio of the exhaust gas, by making use of a phenomenon in which the magnitude of a current flowing through a sensor element changes in accordance with the oxygen concentration of the exhaust gas. In a gas concentration detection apparatus (for example, an ECU (electronic control unit)) connected to the gas sensor, a current detection resistor is connected to the gas sensor so that a current output from the gas sensor flows through the detection resistor. By measuring the potential difference generated across the detection resistor, the oxygen concentration of the exhaust gas is obtained, and the air fuel ratio of the exhaust gas is obtained based on the oxygen concentration. Then, the thus-obtained oxygen concentration or air fuel ratio of the exhaust gas is utilized for air fuel ratio feedback control, which is performed, for example, for adjusting the quantity of fuel injected into the engine.

In recent years, regulation of automotive exhaust gas has become more stringent. In order to meet stricter regulations, there is a need for improved accuracy in performing feedback control of the air fuel ratio near the stoichiometric air fuel ratio (in a stoichiometric range), and in performing feedback control of the air fuel ratio within a predetermined lean range. In a general gas concentration detection apparatus, a voltage output from a detection resistor is converted to digital data, which in turn is input to a CPU so as to perform air fuel ratio feedback control under software control. In general, the gas concentration detection apparatus is configured such that an entire range within which the air fuel ratio varies corresponds to an entire voltage range within which the output voltage of the detection resistor can be accommodated for digital conversion. Therefore, a voltage range assigned to (corresponding to) the stoichiometric range is narrow as compared with the entire voltage range within which the output voltage of the detection resistor can be input for digital conversion. In a known technique, when the output voltage of the detection resistor enters the stoichiometric range, the output voltage of the detection resistor is amplified such that the voltage range assigned to the stoichiometric range is expanded to the entire voltage range within which the output voltage can be accommodated for digital conversion, to thereby improve the detection accuracy of the air fuel ratio in the stoichiometric range (refer to, for example, Patent Document 1).

[Patent Document 1] Japanese Patent Application Laid-Open (kokai) No. 2006-275628

3. Problems to be Solved by the Invention

However, when a circuit which acquires and amplifies the output voltage (potential difference) of the detection resistor is affected by variations in characteristics of electronic components of the circuit and the temperature characteristics thereof, the detected air fuel ratio may contain an error. Especially, when the output voltage of the detection resistor is amplified in the stoichiometric range, the error is also amplified. Accordingly, there is a need to improve accuracy in detecting the air fuel ratio.

SUMMARY OF THE INVENTION

The present invention has been accomplished in order to solve the above-described problems, and an object thereof is to provide a gas concentration detection apparatus and a gas concentration detection system which can improve the accuracy of detection of the concentration of a specific gas component using a gas sensor.

According to a first aspect, the above object of the present invention has been achieved by providing a gas concentration detection apparatus which detects the concentration of a specific gas component by measuring a current which flows through a gas sensor and whose magnitude changes in accordance with the concentration of the specific gas component, the apparatus comprising a detection resistor through which the current output from the gas sensor flows; differential amplification means having a first input terminal and a second input terminal electrically connected to opposite ends of the detection resistor, respectively, which differential amplification means differentially amplifies a potential difference generated across the detection resistor and outputs the amplified potential difference as a detection voltage; amplification factor setting means which sets an amplification factor at which the potential difference is amplified to one of at least two different amplification factors based on the value of the potential difference; potential equalization means which equalizes potentials of the first input terminal and the second input terminal; acquisition means which acquires a correction voltage for each of the amplification factors, the correction voltage being the detection voltage which is output from the differential amplification means when the potential equalization means equalizes the potentials of the first input terminal and the second input terminal; and concentration calculation means which corrects the detection voltage output from the differential amplification based on the correction voltage corresponding to the amplification factor set in accordance with the detection voltage, and calculates a concentration corresponding value, which corresponds to the concentration of the specific gas component, on the basis of the corrected detection voltage.

In the gas concentration detection apparatus according to the first aspect of the present invention, the concentration of the specific gas component is determined on the basis of the detection voltage which is obtained by differentially amplifying the potential difference generated across the detection resistor, through which the current output from the gas sensor flows. Since at least two different amplification factors can be set for the potential difference generated across the detection resistor, the amplification factor can be set in accordance with the required detection accuracy, whereby the gas concentration can be detected accurately. In some cases, the output detection voltage may contain an error due to electronic components used in the circuit. In view of such an error, the acquisition means acquires, as a correction voltage, the detection voltage in a state where the potentials of the first input terminal and the second input terminal of the differential amplification means connected to opposite ends of the detection resistor are equalized (rendered equal to each other), whereby the potential difference across the detection resistor is forcibly rendered "0." That is, the detection voltage (correction voltage) obtained in this state represents an error (offset) generated by the electronic components alone and does not include the potential difference across the detection resistor. When the gas concentration is detected, the detection voltage is corrected based on the correction voltage, whereby the gas concentration can be detected accurately. Since the correction voltage can be acquired for each of the amplification factors, the accuracy in detecting the gas concentration can be further improved.

The gas concentration detection apparatus according to the first aspect of the present invention acquires the correction voltage as follows. The potentials of the first input terminal and the second input terminal are equalized, and then the detection voltage is acquired as the correction voltage. That is, the correction voltage can be acquired in a state where the current output from the gas sensor is flowing through the detection resistor. Accordingly, the first and second input terminals need not be disconnected from the detection resistor, thereby enabling quick acquisition of the correction voltage.

The gas concentration detection apparatus having the above-described configuration may comprise switch means which is electrically connected between the first input terminal and the second input terminal, and which establishes and breaks electrical connection between the first input terminal and the second input terminal. In this case, the potential equalization means causes the switch means to establish electrical connection between the first input terminal and the second input terminal so as to equalize the potentials of the first input terminal and the second input terminal. By virtue of this configuration, the operation of equalizing the potentials of the first input terminal and the second input terminal can be performed easily and reliably.

The gas concentration detection apparatus having the above-described configuration may comprise determination means which determines whether or not the gas sensor has been activated (i.e., has reached an activation temperature). In this case, preferably, the acquisition means repeatedly acquires the correction voltage for each of the amplification factors during a time period after drive of the gas sensor is started until the determination means determines that the gas sensor has been activated. In this way, the acquisition of the correction voltage is performed by making use of a time period during which the gas sensor is being activated. Therefore, once the gas sensor has been activated, the correction voltage has already been acquired, and, thus, the detection of the concentration of the specific gas component can begin right away. Furthermore, since, as described above, acquisition of the correction voltage is repeatedly performed before activation of the gas sensor has been completed (i.e., before the gas sensor has reached the activation temperature), the correction voltage held at the time of completion of the activation of the gas sensor is the latest correction voltage acquired immediately before activation of the gas sensor has been completed. Therefore, correction can be performed accurately.

A gas concentration detection system according to a second aspect of the present invention comprises a gas sensor configured such that the magnitude of a current flowing through the gas sensor changes in accordance with the concentration of a specific gas component; and the gas concentration detection apparatus according to the first aspect which detects the concentration of the specific gas component on the basis of the current output from the gas sensor. The gas concentration detection system according to the second aspect of the present invention enables setting of the amplification factor in accordance with the required detection accuracy to thereby enable accurate detection of the gas concentration. In addition, since correction of the detection voltage is performed by making use of the correction voltages acquired for each of the amplification factors to which the amplification factor for the differential potential is set, accurate detection of the gas concentration becomes possible.

DESCRIPTION OF REFERENCE SYMBOLS

Figure 1:
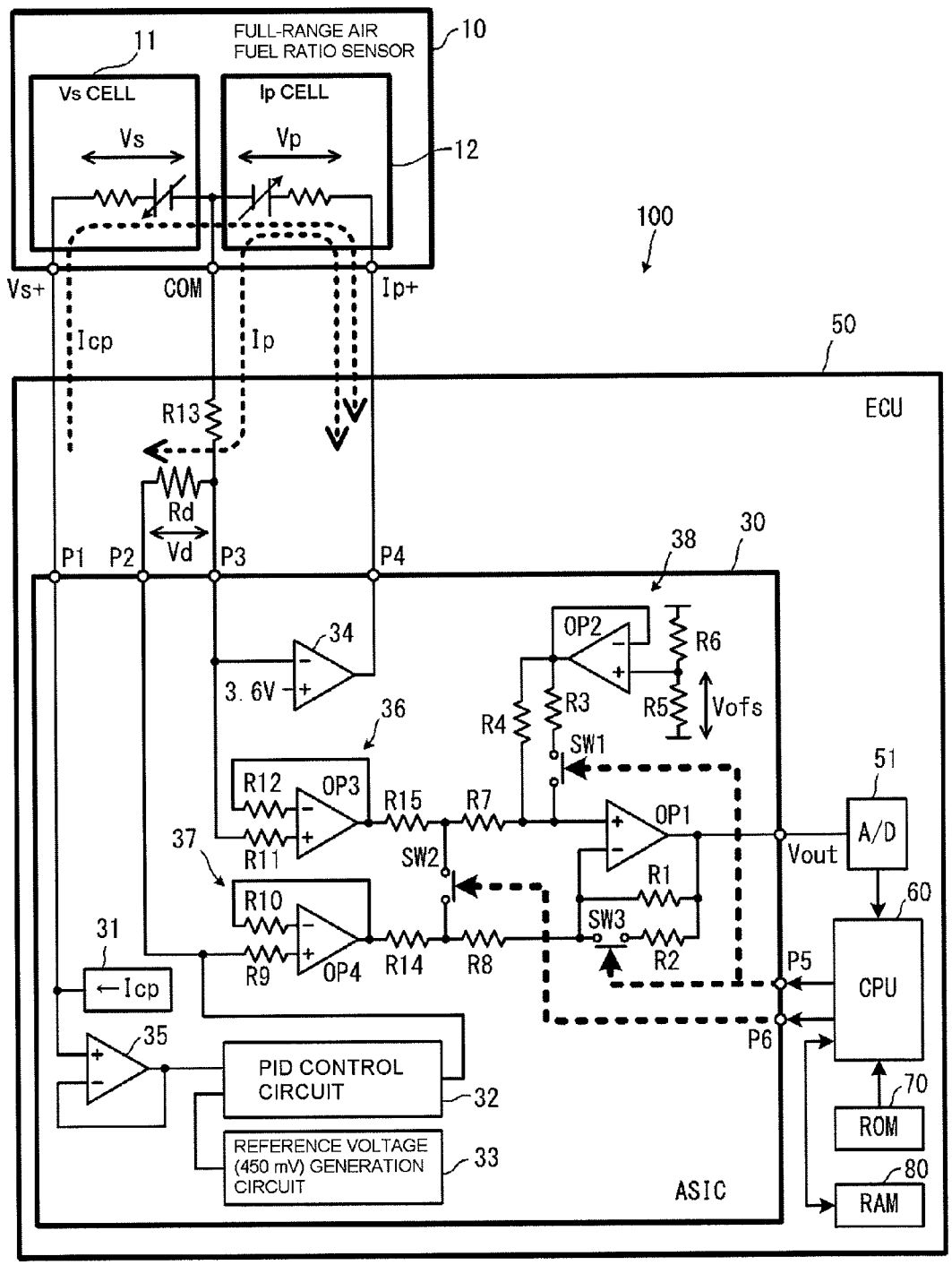
FIG. 1 is a diagram which schematically shows the electrical configuration of the sensor control system 100.

Reference symbols used to identify various elements in the drawings include the following.
10: fall-range air fuel ratio sensor
50: ECU
60: CPU
100: sensor control system
SW1 to SW3: switch
OP1: operational amplifier
Rd: detection resistor

DETAILED DESCRIPTION OF THE PREFERRED EMBODIMENTS

A gas concentration detection apparatus according to an embodiment of the present invention and a gas concentration detection system which includes the gas concentration detection apparatus will now be described with reference to the drawings. However, the present invention should not be construed as being limited thereto. Herein, an ECU (electronic control unit) 50 of an automobile will be described as one example of the gas concentration detection apparatus according to the present invention. Then, a sensor control system 100 which controls a full-range air fuel ratio sensor 10 connected to the ECU 50 in accordance with a gas concentration detection program to be executed by a CPU 60 of the ECU 50 will be described as one example of the gas concentration detection system according to the present invention.

The configuration of the sensor control system 100 will be described with reference to FIG. 1. FIG. 1 is a diagram schematically showing the electrical configuration of the sensor control system 100.

The sensor control system 100 shown in FIG. 1 includes the full-range air fuel ratio sensor 10 and the ECU 50, to which the full-range air fuel ratio sensor 10 is connected. First, the configuration of the full-range air fuel ratio sensor 10 will be described in brief. As is well known to those of ordinary skill in this field of art, the full-range air fuel ratio sensor 10 includes a sensor element built therein which has two types of cells (a Vs cell 11 and an Ip cell 12). Each of the cells has a solid electrolyte body, and electrodes formed on opposite sides thereof. The solid electrolyte body is mainly made of zirconia and has oxygen ion conductivity, and the electrodes are mainly made of Pt. The sensor element is configured such that the Vs cell 11 and the Ip cell 12 are layered to form a small chamber therebetween, into which exhaust gas can be introduced, and respective first electrodes of the cells are exposed to the interior of the small chamber. These first electrodes of the cells are electrically connected to each other, and are connected to a COM port of the full-range air fuel ratio sensor 10. A second electrode of the Vs cell 11 functions as an oxygen reference electrode, which serves as a reference for detecting the oxygen concentration of the exhaust gas introduced into the small chamber, and is connected to a Vs+ port of the full-range air fuel ratio sensor 10. A second electrode of the Ip cell 12 is exposed to the atmosphere outside the sensor element so as to exchange oxygen between the interior of the small chamber and the atmosphere, and is electrically connected to an Ip+ port of the full-range air fuel ratio sensor 10. Since the specific configuration of the sensor element of the full-range air fuel ratio sensor 10 is well known, in FIG. 1, the full-range air fuel ratio sensor 10 is shown in the form of an electrical circuit.

The ECU 50 has a CPU 60, ROM 70, RAM 80, an A/D converter 51, which are well known, and an ASIC (application specific integrated circuit) 30 described below. The A/D converter 51 is connected to a Vout port of the ASIC 30. The A/D converter 51 converts an analog output voltage output from the ASIC 30 through the Vout port to a digital signal, and sends the digital signal to the CPU 60. The ROM 70 stores a gas concentration detection program described below, and initial values of variables, counters, flags, etc. used in the program. The RAM 80 temporarily stores data, and is utilized when the gas concentration detection program is executed. Through execution of the gas concentration detection program, the CPU 60 controls the ASIC 30 so as to detect the oxygen concentration of the exhaust gas by making use of the full-range air fuel ratio sensor 10 and then calculates the air fuel ratio. Furthermore, during execution of the gas concentration detection program, the CPU 60 performs switching control for switches SW1, SW2 and SW3 provided in the ASIC 30. The ECU 50 performs not only the gas concentration detection according to the present embodiment, but also other various controls associated with drive of the automobile. Accordingly, although not illustrated, the ECU 50 has various control circuits for the other various controls, and various control programs, etc., for the other various controls are stored in the ROM 70.

Next, the ASIC 30 will be described. The ASIC 30 is a circuit which is adapted to drive and control the full-range air fuel ratio sensor 10, and is integrated into a single chip so that the ASIC 30 can be easily built in the ECU 50. The ASIC 30 has a plurality of ports P1 to P6 for input and output, the Vout port for outputting an output voltage corresponding to the detected oxygen concentration, an unillustrated port for power supply, etc.

The ASIC 30 includes an Icp supply circuit 31 which supplies a weak current Icp to the Vs cell 11 of the full-range air fuel ratio sensor 10. The Icp supply circuit 31 is connected to the Vs+ port of the full-range air fuel ratio sensor 10 through the P1 port. The current Icp is caused to flow so as to maintain a constant oxygen concentration on the second electrode (the above-described oxygen reference electrode) side of the Vs cell 11.

Furthermore, the ASIC 30 includes an amplifier 34 which supplies a pump current Ip to the Ip cell 12 of the full-range air fuel ratio sensor 10. The inverting input (−) terminal of the amplifier 34 is connected to the P3 port, and is further connected to the COM port of the full-range air fuel ratio sensor 10 through a resistor R13. A reference voltage of 3.6 V is applied to the noninverting input (+) terminal of the amplifier 34. The output terminal of the amplifier 34 is connected to the Ip+ port of the full-range air fuel ratio sensor 10 through the P4 port.

The magnitude of the pump current Ip supplied from the amplifier 34 to the Ip cell 12 is determined by a PID control circuit 32. The input side of the PID control circuit 32 is connected to the P1 port (that is, the Vs+ port of the full-range air fuel ratio sensor 10) through a buffer 35. Furthermore, a reference voltage generation circuit 33 which generates a reference voltage (450 mV), which servers as a control target for the pump current Ip, is connected to the input side of the PID control circuit 32. Meanwhile, the output side of the PID control circuit 32 is connected to the P2 port, and is further connected to the P3 port; that is, the inverting input (−) terminal of the amplifier 34, through a detection resistor Rd described below. The PID control circuit 32 performs feedback control so as to adjust the direction and magnitude of the pump current Ip supplied from the amplifier 34 to the Ip cell 12. In this manner, an electromotive force Vs which is generated as a result of the minute current Icp flowing through the Vs cell 11 becomes 450 mV.

The detection resistor Rd is provided so as to detect the magnitude of the pump current Ip. In the present embodiment, the detection resistor Rd is a resistor having a resistance value of 300Ω and is provided in the ECU 50. Opposite ends of the detection resistor Rd are connected to the P2 port and the P3 port of the ASIC 30. Furthermore, the opposite ends of the detection resistor Rd are connected to the input terminals of an operational amplifier OP1. The operational amplifier OP1 amplifies a potential difference Vd, which is generated across the detection resistor Rd when the pump current Ip flows therethrough, with a predetermined amplification factor, and outputs the amplified potential difference as a detection voltage Vout. Specifically, the P2 port, to which one end of the detection resistor Rd is connected, is connected to the input side of a buffer 37 composed of a resistor R9, a resistor R10 and an operational amplifier OP4. That is, the P2 port is connected to the noninverting input (+) terminal of the operational amplifier OP4 through the resistor R9. The output terminal of the operational amplifier OP4, which is the output side of the buffer 37, is connected to the inverting input (−) terminal thereof through the resistor R10 for negative feedback. The output terminal of the operational amplifier OP4 is also connected to the inverting input (−) terminal of the operational amplifier OP1 through resistors R14 and R8 connected in series. Similarly, the P3 port, to which the other end of the detection resistor Rd is connected, is connected to the input side of a buffer 36 composed of a resistor R11, a resistor R12 and an operational amplifier OP3. That is, the P3 port is connected to the noninverting input (+) terminal of the operational amplifier OP3 through the resistor R11. The output terminal of the operational amplifier OP3, which is the output side of the buffer 36, is also connected to the inverting input (−) terminal thereof through the resistor R12 for negative feedback. The output terminal of the operational amplifier OP3 is also connected to the noninverting input (+) terminal of the operational amplifier OP1 through resistors R15 and R7 connected in series. The operational amplifier OP1 corresponds to the "differential amplification means" in the present invention. Furthermore, the inverting input (−) terminal and the noninverting input (+) terminal of the operational amplifier OP1 correspond to the "first input terminal" and the "second input terminal", respectively, in the present invention.

Furthermore, the output terminal of the operational amplifier OP3 and the output terminal of the operational amplifier OP4 are connected to a switch SW2 through the resistor R15 and resistor R14, respectively. In other words, the connection point between the resistors R15, R7 and the connection point between the resistors R14, R8 are connected to opposite ends of the switch SW2, respectively. The switch SW2 is connected to the CPU 60 through the P6 port, and its ON/OFF state (that is, its close/open state) is controlled during execution of the gas concentration detection program described below. The switch SW2 corresponds to the "switch means" in the present invention.

The operational amplifier OP1 forms an inverting amplifier circuit. As described above, the output terminal of the buffer 36 is connected to the noninverting input (+) terminal of the operational amplifier OP1 through the resistor R15 and resistor R7. Furthermore, the output terminal of a buffer 38 (composed of, for example, an operational amplifier OP2) is connected to the noninverting input (+) terminal of the operational amplifier OP1 through resistors R3 and R4 connected in parallel. Moreover, a switch SW1 is provided between the noninverting input (+) terminal of the operational amplifier OP1 and the resistor R3. The switch SW1 is connected to the CPU 60 through the P5 port, and its ON/OFF state is controlled during execution of the gas concentration detection program described below. Accordingly, the resistance value between the buffer 38 and the operational amplifier OP1 can be switched to the resistance value of the resistor R4 or the combined resistance value of the resistors R4 and R3. The output terminal of the buffer 38 is connected to the inverting input (−) terminal thereof for negative feedback. Meanwhile, an offset voltage is input to the noninverting input (+) terminal of the buffer 38. The offset voltage is a stable voltage Vofs output from the node between resistors R5 and R6, which are connected in series so as to divide an unillustrated power supply voltage and which are adjusted such that the stable voltage Vofs can be obtained.

As described above, the output terminal of the buffer 37 is connected to the inverting input (−) terminal of the operational amplifier OP1 through the resistor R14 and resistor R8. Furthermore, for negative feedback, the output terminal of the operational amplifier OP1 is connected to the inverting input (−) terminal thereof through resistors R1 and R2 connected in parallel. The resistance values of the resistors R14 and R8 are made equal to the resistance values of the resistors R15 and R7, respectively, for matching of input impedance of the operational amplifier OP1. Furthermore, a switch SW3 is provided between the inverting input (−) terminal of the operational amplifier OP1 and the resistor R2. Like the switch SW1, the switch SW3 is connected to the CPU 60 through the P5 port, and its ON/OFF state is synchronized with the switch SW1 during execution of the gas concentration detection program described below. Accordingly, the resistance value of the negatively feedback loop of the operational amplifier OP1 can be switched to the resistance value of the resistor R1 or the combined resistance value of the resistors R1 and R2. Furthermore, since the switch SW1 and the switch SW3 can be switched synchronously with each other, the amplification factor for a potential difference Vd between the opposite ends of the detection resistor Rd, which is differentially amplified by the operational amplifier OP1, can be changed to one of two factors. The resistance values of the resistors R1 and R2 are made equal to the resistance values of the resistors R4 and R3, respectively, for matching of input impedance of the operational amplifier OP1. The output terminal of the operational amplifier OP1 is further connected to the Vout port. The output voltage from the operational amplifier OP1 is converted to a digital signal by the A/D converter 51, and the digital signal is input to the CPU 60.

In the gas concentration detection apparatus (ECU 50) of the present embodiment having the above-described configuration, the oxygen concentration is detected by use of the full-range air fuel ratio sensor 10 in the following manner. In the full-range air fuel ratio sensor 10, the weak current Icp is caused to flow through the Vs cell 11 by the Icp supply circuit 31 provided in the ASIC 30. Thus, oxygen ions move from the first electrode side of the Vs cell 11 (the interior of the small chamber) to the second electrode side of the Vs cell 11. A voltage Vs is generated across the Vs cell 11 as a result of movement of the oxygen ions. The voltage Vs fluctuates, since the amount of the moving oxygen ions changes in accordance with the oxygen concentration of the exhaust gas introduced into the small chamber. Accordingly, the direction and magnitude of the pump current Ip which is caused to flow through the Ip cell 12 is controlled by the PID control circuit 32 so that the voltage Vs coincides with the reference voltage (450 mV which is set as a control target for the voltage Vs for causing the air fuel ratio of the exhaust gas in the small chamber to coincide with the stoichiometric air fuel ratio).

Specifically, in the PID control circuit 32, the difference between the reference voltage (450 mV) generated by the reference voltage generation circuit 33 and the voltage Vs generated across the Vs cell 11 is subjected to a calculation for PID operation, and a resultant signal is fed back to the output of the amplifier 34. When the air fuel ratio of the exhaust gas falls within the rich range and the oxygen concentration in the small chamber is low, the voltage Vs becomes higher than the reference voltage. Therefore, the pump current Ip, whose magnitude corresponds to the potential difference, flows from the PID control circuit 32 and flows through the Ip cell 12 in a direction such that oxygen ions are taken into the interior of the small chamber so as to cause the voltage Vs to approach the reference voltage. On the other hand, when the air fuel ratio of the exhaust gas falls within the lean range and the oxygen concentration in the small chamber is high, the voltage Vs becomes lower than the reference voltage. Therefore, the pump current Ip, whose magnitude corresponds to the potential difference, flows from the amplifier 34 and flows through the Ip cell 12 in the opposite direction such that oxygen ions are taken out of the interior of the small chamber so as to cause the voltage Vs to approach the reference voltage. Accordingly, the oxygen concentration and the air fuel ratio of the exhaust gas introduced into the interior of the small chamber can be detected by detecting the direction and magnitude of the pump current Ip. Since the pump current Ip flows through the detection resistor Rd, the direction and magnitude of the pump current Ip can be detected by measuring the potential difference Vd generated across the detection resistor Rd.

As described above, the opposite ends of the detection resistor Rd are connected to the input terminals of the operational amplifier OP1 through the buffer 36 and the resistors R15 and R7, and the buffer 37 and the resistors R14 and R8, respectively. This operational amplifier OP1 forms an inverting amplifier circuit which differentially amplifies the potential difference Vd generated across the detection resistor Rd in accordance with the pump current Ip. Accordingly, the amplification factor of the operational amplifier OP1 is determined by the ratio of the combined resistance value of the resistors R1 and R2 to the combined resistance value of the resistors R14 and R8 when the switch SW3 is ON, and is determined by the ratio of the resistance value of the resistor R1 to the combined resistance value of the resistors R14 and R8 when the switch SW3 is OFF. In the present embodiment, the amplification factor for the potential difference is set to 1 and 4.5; and the resistance values of the resistors R1, R2, R8 and R14 are determined to satisfy this requirement. Furthermore, as described above, the resistors R3, R4, R7 and R15 are provided for matching of input impedance of the operational amplifier OP1. Accordingly, the resistance values of the resistors R3, R4, R7 and R15 are made equal to the resistance values of the resistors R1, R2, R8 and R14, respectively, and the switch SW1 is switched synchronously with the switch SW3.

Since the offset voltage input through the buffer 38 is superposed on the output of the operational amplifier OP1, the output of the operational amplifier OP1 is offset to the positive side by an amount corresponding to the voltage Vofs. In the present embodiment, the voltage Vofs is set to 2.3 V. As described above, since the polarity of the pump current Ip changes between positive and negative, the voltage Vofs is superposed on the output voltage (detection voltage) Vout of the operational amplifier OP1, as shown in the following mathematical formula (1). That is, the detection voltage Vout is offset by the voltage Vofs such that the range of the detection voltage Vout coincides with a voltage range within which the CPU 60 can accommodate the detection voltage Vout (in general, a voltage within a range of 0 to 5 V is converted to a digital value by the A/D converter 51).

(the detection voltage $V$out)=(the current value of the pump current $I$p)×(the resistance value of the detection resistor $R$d)×(the amplification factor)+ (the offset voltage $V$ofs)     (1)

In the present embodiment, as described above, the amplification factor can be switched to 1 or 4.5, and a resistor having a resistance value of 300Ω is used for the detection resistor Rd, and the offset voltage Vofs is set to 2.3 V.

Figure 2:
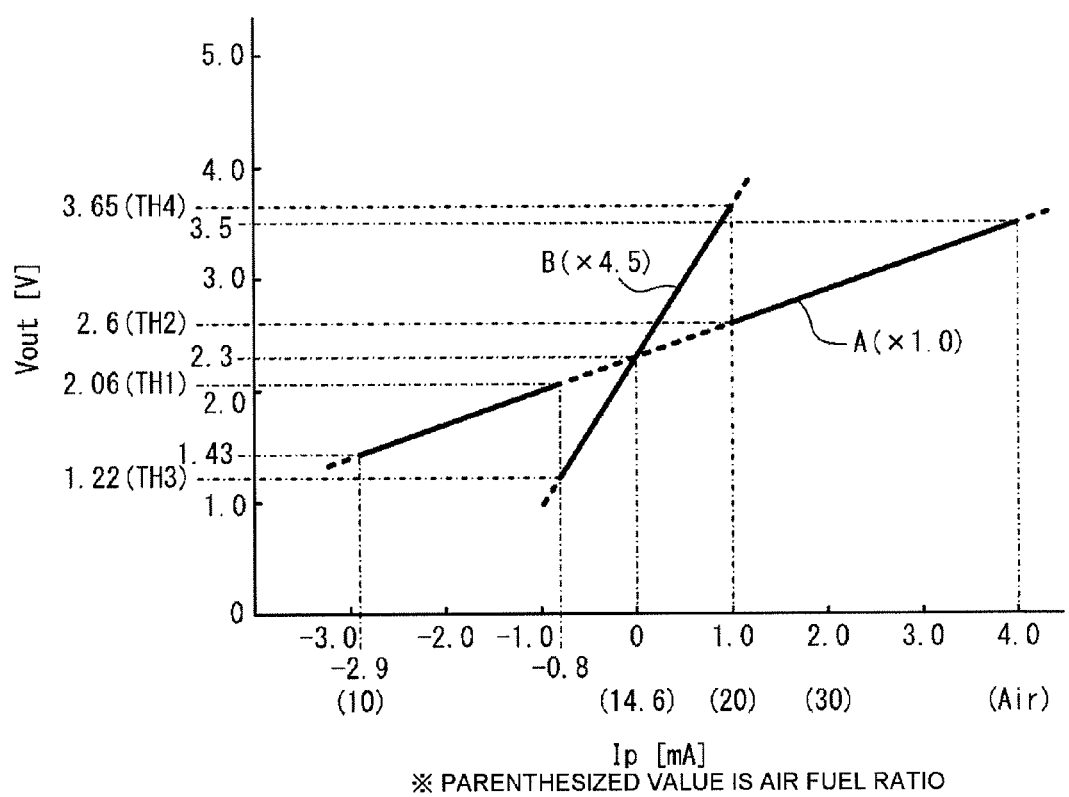
FIG. 2 is a graph showing the relationship between the detection voltage Vout and the pump current Ip.

When the amplification factor is set to 1, the relation between the detection voltage Vout and the current value of the pump current Ip represented by the mathematical formula (1) is linear; that is, the detection voltage Vout changes linearly with respect to the current value of the pump current Ip at least when the current value of the pump current Ip falls within a range of −2.9 mA to 4.0 mA, as shown by a straight line A in a graph of FIG. 2. Specifically, when the detection voltage Vout is 1.43 V, the current value of the pump current Ip is −2.9 mA. In this case, the air fuel ratio of the exhaust gas is determined to be 10 by reference to an unillustrated table. When the detection voltage Vout is 3.5 V, the current value of the pump current Ip is 4.0 mA. In this case, the air fuel ratio of the exhaust gas is determined to be α (Air) by reference to the unillustrated table. When the current value of the pump current Ip is 0 mA, the offset voltage (the voltage Vofs) is output as the detection voltage Vout. In this case, the air fuel ratio is 14.6, and the exhaust gas has a stoichiometric air fuel ratio (stoichiometric state).

In order to detect more accurately a variation in the current value of the pump current Ip near a current value corresponding to the stoichiometric air fuel ratio, in the present embodiment, a range in which the current value of the pump current Ip is near 0 mA (specifically, from −0.8 mA to 1.0 mA) is defined as a stoichiometric range. Then, when the value of the detection voltage Vout enters the stoichiometric range, the amplification factor of the operational amplifier OP1 is changed so that the output voltage becomes 4.5 times. Thus, a slight change in the detection voltage Vout can be easily detected in the stoichiometric range, whereby the detection accuracy of the full-range air fuel ratio sensor 10 for the oxygen concentration in the stoichiometric range can be improved.

More specifically, when the amplification factor is set to 4.5 in the stoichiometric range, the relation between the detection voltage Vout and the current value of the pump current Ip represented by the mathematical formula (1) is illustrated by a straight line B in the graph of FIG. 2. In the case where the current value of the pump current Ip is −0.8 mA, the detection voltage Vout is 2.06 V when the amplification factor is set to 1, but the detection voltage Vout becomes 1.22 V when the amplification factor is set to 4.5. Meanwhile, in the case where the current value of the pump current Ip is 1.0 mA, the detection voltage Vout is 2.60 V when the amplification factor is set to 1, but the detection voltage Vout becomes 3.65 V when the amplification factor is set to 4.5. That is, within the stoichiometric range, the detection voltage Vout varies within a range of 2.06 V to 2.60 V when the amplification factor is set to 1, but this variation is amplified such that the detection voltage Vout varies within a range of 1.22 V to 3.65 V when the amplification factor is set to 4.5.

The changing of the amplification factor associated with acquisition of the detection voltage Vout is effected when the measurement mode is switched between a wide-range measurement mode and a stoichiometric measurement mode in the gas concentration detection program described below. In the wide-range measurement mode, the amplification factor is set to 1. In the stoichiometric measurement mode, the amplification factor is set to 4.5. Incidentally, due to variation in the characteristics of electronic components of the gas concentration detection apparatus and the temperature characteristics thereof, an error is produced in the course of detecting the potential difference Vd generated across the detection resistor Rd. Since the error is exaggerated when the amplification factor is rendered higher, the gas concentration detection apparatus of the present embodiment performs different corrections in accordance with the amplification factor, whereby the detection accuracy is improved further.

Figure 3:
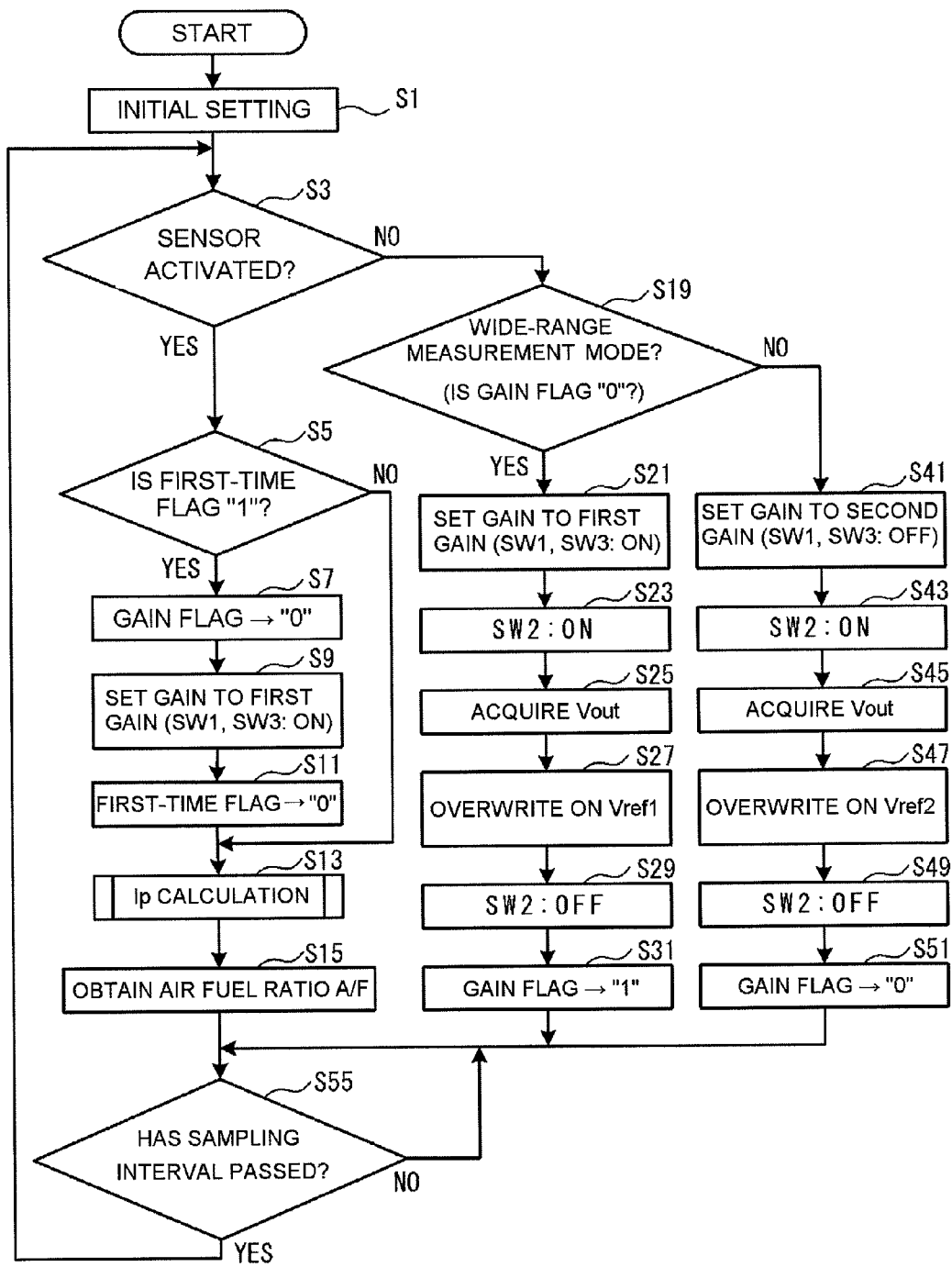
FIG. 3 is a flowchart showing the main routine of the gas concentration detection program.
Figure 4:
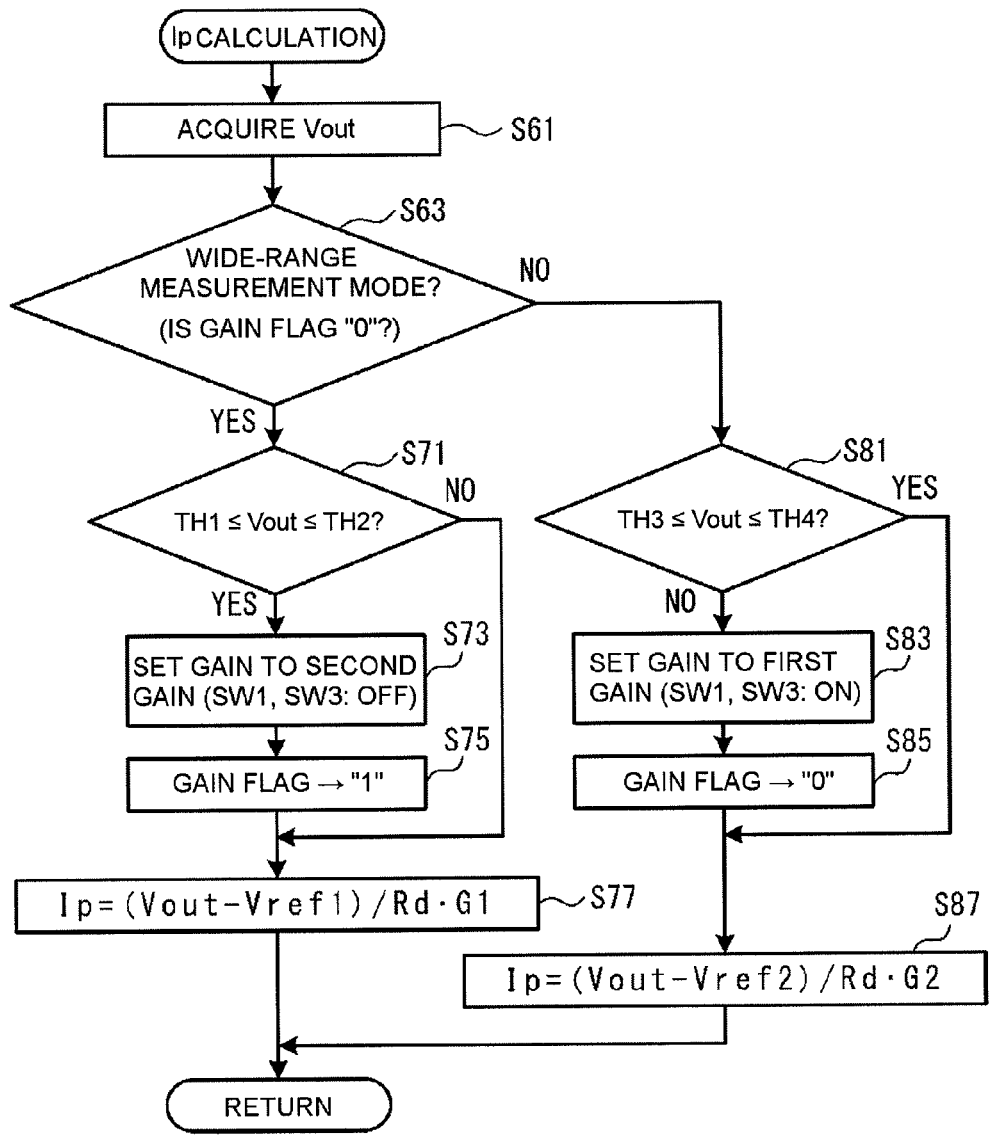
FIG. 4 is a flowchart showing the Ip calculation processing which is called from the main routine of the gas concentration detection program.

Processing for the correction is performed when the gas concentration detection program is executed. Briefly, during a period between the start of drive of the full-range air fuel ratio sensor 10 and the completion of the activation of the full-range air fuel ratio sensor 10, a correction value (a correction voltage described below) is acquired. The correction value is used to cancel the influence of an error when the differential voltage is amplified at each of the amplification factors in acquiring the detection voltage Vout. Then, after activation of the full-range air fuel ratio sensor 10 is complete, a correction corresponding to each amplification factor is performed when the detection voltage Vout is acquired, whereby the gas concentration can be detected accurately. Hereinafter, the gas concentration detection program will be described with reference to FIG. 3 and FIG. 4. FIG. 3 is a flowchart showing the main routine of the gas concentration detection program. FIG. 4 is a flowchart showing Ip calculation processing which is called from the main routine of the gas concentration detection program. Each step in these flowcharts is abbreviated to "S."

First, various variables, flags, counters, etc., which are used in the gas concentration detection program will be described. A "first-time" flag is a flag which is used to check whether or not calculation of the pump current Ip is performed for the first time after completing activation of the full-range air fuel ratio sensor 10. This checking is performed so as to apply various settings when the calculation of the pump current Ip is performed for the first time after completing activation. If the value of the flag is "1", the flag indicates that the calculation of the pump current Ip has not yet been performed. A "gain" flag is a flag which is used to check whether the current measurement mode is the "wide-range measurement mode," in which the amplification factor associated with detection of the gas concentration is set to 1, or the "stoichiometric measurement mode," in which the amplification factor associated with detection of the gas concentration is set to 4.5. If the value of the flag is "0," the flag indicates that the current measurement mode is the wide-range measurement mode. If the value of the flag is "1," the flag indicates that the current measurement mode is the stoichiometric measurement mode. A constant "G1" is an amplification factor used in the wide-range measurement mode, and "1" is set as the constant "G1." A constant "G2" is the amplification factor used in the stoichiometric measurement mode, and "4.5" is set as the constant "G2." Constants "TH1," "TH2," "TH3" and "TH4" are threshold values to be compared with the detection voltage Vout so as to switch the measurement mode between the wide-range measurement mode and the stoichiometric measurement mode. In the present embodiment, "2.06," "2.6," "1.22" and "3.65" (V) are set as the constants "TH1," "TH2," "TH3," and "TH4," respectively.

A variable "Vout" is a digital value which is obtained through A/D conversion of the output of the operational amplifier OP1 and acquired by the CPU 60. The output of the operational amplifier OP1, which is an analog voltage within the range of 0 to 5 V, is handled as a digital value of 256 levels in the processing of the gas concentration detection program. However, in order to facilitate description and understanding, the processing of the gas concentration detection program will be described under the assumption that the variable "Vout" represents the analog voltage before being subjected to A/D conversion. This convention also applies to the above-described TH1, TH2, TH3 and TH4, as well as to Vref1 and Vref2, described below. The variables "Vref1" and "Vref2" are digital values which are obtained by A/D conversion of measurement values of the offset voltage Vofs, measured with the amplification factor set to 1 and 4.5, respectively, and which are acquired by the CPU 60. As described below, the variables Vref1 and Vref2 are acquired as correction voltages each being equal to a voltage obtained by adding an error caused by the electronic components to the offset voltage Vofs. Therefore, use of the variables Vref1 and Vref2 for correction at the time of the Ip calculation eliminates influence of the error. A constant "Rd" is the resistance value of the detection resistor Rd, and is used in the Ip calculation. A variable "Ip" is a variable which represents the pump current Ip flowing through the detection resistor Rd. The pump current Ip is calculated based on the detected potential difference Vd generated across the detection resistor Rd (that is, based on Vout, which is obtained as the output of the operational amplifier OP1), and is stored as the variable "Ip." That is, the current value of the pump current Ip is computed in accordance with the above-described mathematical formula (1), and is stored as the variable Ip. A "sampling interval" counter is a counter used for clocking a wait time corresponding to a sampling interval to thereby enable the CPU to repeatedly execute a series of processing steps of the main routine of the gas concentration detection program every time a fixed time (for example, 10 msec) elapses.

The above-described constants are previously stored in the ROM 70 together with the gas concentration detection program. Although not illustrated, a table (or an arithmetic expression) for obtaining an air fuel ratio corresponding to the calculated Ip is also stored in the ROM 70. The storage areas for the above-described respective flags, counters, and variables are secured in the RAM 80 when the gas concentration detection program is executed.

Next, operation of the gas concentration detection program will be described. When the main routine of the gas concentration detection program shown in FIG. 3 is executed in response to startup of the automobile, first, the initial setting is performed, whereby the variables, flags, counters, etc., are set to initial values or reset (S1). The gain flag is set to "0" (the wide-range measurement mode), and "1" is stored in the first-time flag. Furthermore, 2.3 V (the offset voltage Vofs which contains no error component; an initial value) is stored as Vref1 and Vref2. Furthermore, clocking of the time corresponding to the sampling interval is started.

Next, a determination is made as to whether or not activation of the full-range air fuel ratio sensor 10 is complete (S3). The determination for checking whether or not activation is complete is performed on the basis of a signal obtained from an unillustrated activation determination circuit. Before activation of the full-range air fuel ratio sensor 10 is complete (S3: NO), processing of S19 to S51 is repeatedly performed each time the corresponding sampling interval (10 msec.) elapses. The CPU 60, which determines in S3 whether or not activation of the full-range air fuel ratio sensor 10 is complete, corresponds to the "determination means" in the present invention. The activation determination circuit detects an impedance of Vs cell 11 and outputs a signal indicating activation of the full-range air fuel ratio sensor 10 when the impedance falls below a threshold value. It is possible to employ, as the activation determination circuit, the circuit disclosed in US Patent published Application No. 2007/0119437, incorporated herein by reference.

In S19, a determination as to whether or not the wide-range measurement mode is in effect is made by reference to the gain flag (S19). When this processing is executed for the first time, the gain flag is reset to "0" in the initial setting (S1) (S19: YES). Therefore, the instant mode is determined to be the wide-range measurement mode, and the target gain is set to a first gain (that is, the amplification factor of the operational amplifier OP1 is set to 1) (S21). Specifically, a signal is output for turning ON both the switches SW1 and SW3 in FIG. 1. As a result, the amplification factor of the operational amplifier OP1 is set to 1 (=(the combined resistance value of the resistors R1 and R2)/(the combined resistance value of the resistors R8 and R14)).

Next, a signal for turning ON the switch SW2 is output (S23). As described above, the opposite ends of the switch SW2 are connected to the inverting input (−) terminal and the noninverting input (+) terminal of the operational amplifier OP1, respectively. As a result, electrical connection is established between the two terminals, whereby the potentials of the terminals are equalized. Since the operational amplifier OP1 forms a differential amplifier circuit, the output thereof or the detection voltage Vout becomes equal to the offset voltage (that is, the voltage Vofs) which is input through the buffer 38. This output may contain an error (such that the output of OP1 is different from Vofs) attributable to the resistors R1 to R4, the components contained in the buffer 38 and the operational amplifier OP1, etc. The CPU 60 acquires, through the A/D converter 51, the detection voltage Vout in a state in which the target gain is set to the first gain (S25), and stores the detection voltage Vout as Vref1 (S27). The CPU 60, which turns ON the switch SW2 in S23 or S43 described below so as to establish electrical connection between the inverting input (−) terminal and the noninverting input (+) terminal of the operational amplifier OP1 to thereby equalize the potentials thereof, corresponds to the "potential equalization means" in the present invention. The CPU 60, which acquires the detection voltage Vout in S25 or S45 described below, and obtains the correction voltages Vref1 and Vref2 for the respective amplification factors, corresponds to the "acquisition means" in the present invention.

Afterwards, a signal for turning OFF the switch SW2 is output (S29) so as to break the electrical connection between the inverting input (−) terminal and the noninverting input (+) terminal of the operational amplifier OP1. Then, "1" is stored in the gain flag (S31), and the processing proceeds to S55. In S55, a determination is made as to whether or not the time corresponding to the sampling interval has elapsed. The processing waits until 10 msec has elapsed after the start of the clocking (S55: NO). When 10 msec has elapsed (S55: YES), the processing returns to S3. Then, the clocking of the time corresponding to the sampling interval is reset.

In S3, a determination is again made as to whether or not activation of the full-range air fuel ratio sensor 10 is complete. If activation of the full-range air fuel ratio sensor 10 is not complete, as in the above-described case, the processing proceeds to S19. Since the gain flag was set to "1" in S31 and the measurement mode was set to the stoichiometric measurement mode in the previous operation cycle (S19: NO), the target gain is set to a second gain (that is, the amplification factor of the operational amplifier OP1 is set to 4.5) (S41). Specifically, a signal for turning OFF both the switches SW1 and SW3 in FIG. 2 is output. As a result, the amplification factor of the operational amplifier OP1 is set to 4.5 (=(the resistance value of the resistor R1)/(the combined resistance value of the resistors R8 and R14)). The CPU 60, which turns ON the switches SW1 and SW3 in S21 so as to set the amplification factor to 1 and turns OFF the switches SW1 and SW3 in S41 so as to set the amplification factor to 4.5, corresponds to the "amplification factor setting means" in the present invention.

Next, as in the above-described case, a signal for turning ON the switch SW2 is output (S43). The output (detection voltage Vout) of the operational amplifier OP1 in the stoichiometric measurement mode may contain an error attributable to the resistors R1 and R3, components contained in the buffer 38 and the operational amplifier OP1, etc. The CPU 60 acquires, through the A/D converter 51, the detection voltage Vout in a state in which the target gain is set to the second gain (S45), and stores the detection voltage Vout as Vref2 (S47). Afterwards, a signal for turning OFF the switch SW2 is output (S49), and "0" is stored in the gain flag this time (S51). Then, the processing proceeds to S55. When the time corresponding to the sampling interval has elapsed (S55: YES), the processing returns to S3.

In this way, until activation of the full-range air fuel ratio sensor 10 is complete, the processing of S19 to S51 is repeatedly executed each time the corresponding sampling interval elapses. Vref1 and Vref2 are overwritten by the value of Vout output when the gain is set to the first gain and the value of Vout output when the gain is set to the second gain, respectively, which are newly acquired each time S27 and S47 are executed, respectively, whereby Vref1 and Vref2 are updated to the latest correction voltages as of that point in time.

Then, after activation of the full-range air fuel ratio sensor 10 is complete (S3: YES), processing of S5 to S15 is repeatedly performed each time the corresponding sampling interval (10 msec.) elapses. First, in S5, a determination is made as to whether or not the processing of S5 is executed for the first time after activation of the full-range air fuel ratio sensor 10 is complete. If the processing is being executed for the first time (S5: YES), processing of S7 to S11 is executed so as to perform various settings. In S7, "0" is stored in the gain flag, whereby the measurement mode is set to the wide-range measurement mode irrespective of the measurement mode before activation of the full-range air fuel ratio sensor 10 is complete. Then, the target gain is set to the first gain, and a signal for turning ON the switches SW1 and SW3 is output so as to set the amplification factor of the operational amplifier OP1 to 1 (S9). Then, "0" is stored in the first-time flag (S11) so that, in the next and subsequent operation cycles, a "NO" determination is made in S5 and the processing of S7 to S11 is not executed. The processing then proceeds to S13.

In S13, the subroutine of the Ip calculation processing of FIG. 4 is called. As shown in FIG. 4, in the Ip calculation processing, the output (the detection voltage Vout) of the operational amplifier OP1 is acquired (S61). Since the switch SW2 shown in FIG. 2 is OFF, the operational amplifier OP1 outputs a voltage which is obtained by differentially amplifying the potential difference Vd across the detection resistor Rd, and on which the offset voltage (the voltage Vofs) is superimposed. Since the target gain is set to the first gain when the Ip calculation processing is executed for the first time, the amplification factor of the operational amplifier OP1 is 1. The detection voltage Vout, which is an analog value, is converted to a digital value, and the digital value is stored as the variable Vout.

Next, a determination as to whether or not the wide-range measurement mode is in effect is made by reference to the gain flag (S63). When this processing is executed for the first time, the gain flag is reset to "0" in S7 (S63: YES). Therefore, at the instant point in time, the current measurement mode is the wide-range measurement mode. Next, in S71, a determination is made as to whether or not the instant value of Vout in the wide-range measurement mode falls within the stoichiometric range. That is, if Vout assumes a value which falls within a range of TH1 to TH2 inclusive (S71: YES), in order to acquire the detection voltage Vout in the stoichiometric measurement mode in the next operation cycle, the target gain is set to the second gain and the switches SW1 and SW3 are turned OFF (S73); and the processing for setting the gain flag to "1" is performed (S75). After that, the processing proceeds to S77. In this way, the switches SW1 and SW3 are switched in advance for the next detection operation. Therefore, it is not necessary to wait until the output of the operational amplifier OP1 becomes stable when the detection is performed in the next operation cycle. On the other hand, if Vout is lower than TH1 or higher than TH2 (S71: NO), the processing proceeds directly to S77 since the detection voltage Vout must be acquired in the wide-range measurement mode in the next operation cycle.

Specifically, if the value which Vout can assume in the wide-range measurement mode (indicated by the straight line A in FIG. 2) is lower than TH1 (2.06 V) or higher than TH2 (2.6 V), since the value falls outside the stoichiometric range (in which the current value of the pump current Ip is near 0 mA; that is, falls within a range of −0.8 mA to 1.0 mA), the wide-range measurement mode is continued. Meanwhile, if the value of Vout falls within the range of TH1 (2.06 V) to TH2 (2.6 V), the measurement mode is set to the stoichiometric measurement mode, so that acquisition of the detection voltage Vout in the next operation cycle can be performed in a high-accuracy state in which the amplification factor is set to 4.5.

Returning to FIG. 4, next, in S77, the pump current Ip is calculated. That is, the current value of the pump current Ip is obtained in accordance with the mathematical formula (1); (the current value of the pump current Ip)={(the detection voltage Vout)−(the offset voltage Vofs)}/{(the resistance value of the detection resistor Rd)×(the amplification factor)}. The detection voltage Vout contains the above-described measurement error. However, the pump current Ip for the case where the gain is set to the first gain (the amplification factor is set to 1) can be accurately obtained by means of eliminating the influence of the measurement error by making use of the correction voltage which is acquired in a state in which the measurement error is superposed on the offset voltage Vofs. That is, the pump current Ip for the above-mentioned case can be accurately obtained by making use of a mathematical formula "Ip=(Vout−Vref1)/Rd·G1." In S77, the value of the pump current Ip which is obtained by making use of the mathematical formula is stored as the variable Ip. The processing then returns to the main routine.

In the main routine of the gas concentration detection program shown in FIG. 3, an air fuel ratio A/F is obtained in subsequent S15. That is, an air fuel ratio corresponding to Ip is obtained by reference to an unillustrated table. For example, the thus-obtained air fuel ratio is used for feedback control to determine the fuel injection quantity in another program executed by the CPU 60 (in some cases, Ip may be used as is). Then, after the processing returns to S3 via S55, the processing of S5 to S15 is repeatedly executed each time the sampling interval elapses, and each time the pump current Ip and the air fuel ratio A/F are obtained. The CPU 60, which obtains the air fuel ratio A/F as a concentration corresponding value (corresponding to the oxygen concentration of the exhaust gas) in S15 on the basis of the pump current Ip calculated in S77 and S87, corresponds to the "concentration calculation means" in the present invention.

In the Ip calculation processing shown in FIG. 4, when the Ip calculation processing is executed again in an operation cycle subsequent to the operation cycle in which the measurement mode is changed from the wide-range measurement mode to the stoichiometric measurement mode, the gain flag is "1" (S63: NO). Therefore, the processing proceeds to S81. In S81, a determination is made as to whether or not the instant value of Vout in the stoichiometric measurement mode falls outside the stoichiometric range. That is, if Vout falls within the range of TH3 to TH4 inclusive (S81: YES), the processing proceeds directly to S87, because the detection voltage Vout must be acquired in the stoichiometric measurement mode in the next operation cycle. Meanwhile, if Vout is lower than TH3 or higher than TH4 (S81: NO), in order to acquire the detection voltage Vout in the wide-range measurement mode in the next operation cycle, as in the above-described case, the target gain is set to the first gain and the switches SW1 and SW3 are turned ON (S83); and processing for setting the gain flag to "0" is performed (S85). Thereafter, the processing proceeds to S87.

Specifically, if the value which Vout can assume in the stoichiometric measurement mode (indicated by the straight line B in FIG. 2) is lower than TH3 (1.22 V) or higher than TH4 (3.65 V), the value falls outside the stoichiometric range. Therefore, the measurement mode is switched to the wide-range measurement mode. Meanwhile, if the value of Vout falls within the range of TH3 (1.22 V) to TH4 (3.65 V) inclusive, the stoichiometric measurement mode is continued so that acquisition of the detection voltage Vout in the next operation cycle is performed in a high-accuracy state in which the amplification factor is set to 4.5.

Returning to FIG. 4, next, in S87, the pump current Ip is calculated. As in the above-described case, the detection voltage Vout contains a measurement error. However, the pump current Ip for the case where the gain is set to the second gain (the amplification factor is set to 4.5) can be accurately obtained by eliminating the influence of the measurement error. This is done by making use of the correction voltage which is acquired in a state in which the measurement error is superposed on the offset voltage Vofs. That is, the pump current Ip for the above-mentioned case can be accurately obtained by using the mathematical formula "Ip=(Vout−Vref2)/Rd·G2." In S87, the value of the pump current Ip which is obtained using the mathematical formula is stored as the variable Ip. The processing then returns to the main routine of FIG. 3 so as to obtain the air fuel ratio A/F (S15). Hereinafter, similarly, the processing of S5 to S15 is repeatedly executed each time the sampling interval elapses, and each time the pump current Ip and the air fuel ratio A/F are obtained.

The present invention is not limited to the above embodiment, and various modifications and changes can be made within the spirit and scope of the claims appended hereto. For example, the resistance value of the detection resistor Rd and the values of the threshold values TH1 to TH4 used for changeover between the wide-range measurement mode and the stoichiometric measurement mode may be set to conform to the characteristics of the sensor element of the full-range air fuel ratio sensor 10. The sampling interval is not limited to 10 msec, and may be arbitrarily set. Furthermore, the amplification factor of the operational amplifier OP1 may be arbitrarily set. In the above embodiment, the number of selectable amplification factors is two; however, the number of selectable amplification factors may be three or more.

In the above embodiment, the pump current Ip is calculated in S77 and S87, the air fuel ratio is obtained from the pump current Ip in S15, and the air fuel ratio is utilized for the air fuel ratio feedback control in another program. However, the above embodiment may be modified such that the oxygen concentration is obtained on the basis of the pump current Ip, and the thus obtained oxygen concentration is used for the air fuel ratio feedback control in another program. Alternatively, the above embodiment may be modified such that the pump current Ip is utilized for the air fuel ratio feedback control in another program as a concentration corresponding value which corresponds to the oxygen concentration.

In the above embodiment, electrical connection between the inverting input (−) terminal and the noninverting input (+) terminal of the operational amplifier OP1 is established and broken by mean of controlling the ON/OFF state of the SW2. However, the above embodiment may be modified such that the outputs of the buffers 36 and 37 are brought into a high-impedance state so as to equalize the potentials of the two terminals of the operational amplifier OP1.

This application is based on Japanese Patent Application No. JP 2008-218738 filed Aug. 27, 2008, incorporated herein by reference in its entirety.

The invention claimed is:

1. A gas concentration detection apparatus which detects the concentration of a specific gas component by measuring a current which flows through a gas sensor and whose magnitude changes in accordance with the concentration of the specific gas component, the apparatus comprising:

a detection resistor through which the current output from the gas sensor flows;

differential amplification means having a first input terminal and a second input terminal electrically connected to opposite ends of the detection resistor, respectively, which differential amplification means differentially amplifies a potential difference generated across the detection resistor and outputs the amplified potential difference as a detection voltage;

amplification factor setting means which sets an amplification factor at which the potential difference is amplified to one of at least two different amplification factors based on the value of the potential difference;

potential equalization means which equalizes potentials of the first input terminal and the second input terminal;

acquisition means which acquires a correction voltage for each of the amplification factors, the correction voltage being the detection voltage which is output from the differential amplification means when the potential equalization means equalizes the potentials of the first input terminal and the second input terminal; and concentration calculation means which corrects the detection voltage output from the differential amplification means based on the correction voltage corresponding to the amplification factor set in accordance with the detection voltage, and calculates a concentration corresponding value, which corresponds to the concentration of the specific gas component, on the basis of the corrected detection voltage.

2. The gas concentration detection apparatus according to claim 1, further comprising switch means electrically connected between the first input terminal and the second input terminal, and which establishes and breaks electrical connection between the first input terminal and the second input terminal, wherein the potential equalization means causes the switch means to establish electrical connection between the first input terminal and the second input terminal so as to equalize the potentials of the first input terminal and the second input terminal.

3. The gas concentration detection apparatus according to claim 1, further comprising determination means which determines whether or not the gas sensor is activated, wherein the acquisition means repeatedly performs the operation of acquiring the correction voltage for each of the amplification factors during a time period after drive of the gas sensor is started until the determination means determines that the gas sensor is activated.

4. A gas concentration detection system comprising:

a gas sensor configured such that the magnitude of a current flowing through the gas sensor changes in accordance with the concentration of a specific gas component; and the gas concentration detection apparatus as claimed in claim 1 which detects the concentration of the specific gas component on the basis of the current output from the gas sensor.

* * * * *